United States Patent [19]

Driscoll

[11] 3,933,432

[45] Jan. 20, 1976

[54] PHOTOIONIZATION

[75] Inventor: John N. Driscoll, Revere, Mass.

[73] Assignee: HNU Systems Inc., Newton Upper Falls, Mass.

[22] Filed: Oct. 29, 1974

[21] Appl. No.: 518,231

[52] U.S. Cl. .............. 23/232 E; 23/254 E; 250/423
[51] Int. Cl.² ..................... G01N 21/26; H01J 27/00
[58] Field of Search .......... 23/232 E, 232 R, 232 C, 23/254 R, 254 E, 255 R, 255 E; 250/423, 424

[56] References Cited
UNITED STATES PATENTS

| | | | |
|---|---|---|---|
| 2,583,541 | 1/1952 | Berry | 250/424 |
| 3,540,851 | 11/1970 | Vree et al. | 23/232 R |
| 3,607,084 | 9/1971 | Mackey et al. | 23/254 E |

OTHER PUBLICATIONS

Poschenrieder, W., et al., J. Applied Physics, 37, No. 7, June 1966, pp. 2812–2820.

Primary Examiner—Robert M. Reese

[57] ABSTRACT

Apparatus for and method of photoinization in which a gas permeable membrane is extended across a chamber in a housing dividing said chamber into two subchambers, a ballast chamber having a gas inlet and a gas outlet on one side of said membrane, and a photoionization chamber having detection electrodes and a radiation source on the other side of said membrane, gases from a sample stream being diffused into said photoionization chamber through said membrane.

25 Claims, 4 Drawing Figures

PHOTOIONIZATION

This invention relates to improved photoionization apparatus and methods.

It is a principal object of this invention to permit the use of a sealed radiation source for photoionization of a component of a gaseous stream without affecting instrument sensitivity by the deposit of particulate matter on the radiation transmitting surface exposed to the photoionization chamber. It is a further object of this invention to selectively remove interfering species from the gaseous stream thereby to permit detection with improved specificity of a predetermined component of the gaseous stream. It is yet a further object of this invention to compensate for interference of varying oxygen content in gaseous streams.

In general this invention features a housing having a chamber therein, gas inlet and outlet passages communicating with the chamber, a radiation source exposed to the chamber and detection electrodes in the chamber. A gas permeable membrane extends across the chamber dividing it into a ballast chamber on one side of the membrane, the gas inelt and outlet communicating therewith, and a photoionization chamber on the other side of the membrane, the radiation source exposed thereto and the electrodes positioned therein. Gases from a gaseous stream flow from the inlet through the ballast chamber and exit through the outlet. A portion of the gases is diffused through the membrane into the photoionization chamber where it is exposed to radiant energy from the radiation source an ionization of a component of the stream is detected at the electrodes.

In particular embodiments of the invention a purge gas passage communicates with the photoionization chamber. The inlet passage and the purge gas passage each have connected in series therewith a combustion chamber and heating means therefor in which the combustion chamber contains a catalyst, e.g., platinum, effective for the conversion of hydrocarbons to non-interfering species. The inlet passage and the purge gas passage each also have connected in series therewith a radiation source for the conversion of oxygen to ozone. A branch conduit is connected to the conduit carrying the gaseous stream to the inlet passage. Heating means are provided adjacent the inlet and outlet passages.

In the detection of an inorganic component in the effluent gaseous steam, where interference from hydrocarbon species may be anticipated, prior to passing the gases into the photoionization chamber the gases are first contacted with a heated catalyst, preferably platinum, to convert the hydrocarbons to non-interfering species. When air is used as a purge gas in the photoionization chamber, it similarly may first be passed over a heated catalyst to convert any hydrocarbons present therein to non-interfering species.

In the detection of ammonia in the presence of nitric oxide, ozone is introduced into the gases and is reacted with the nitric oxide to remove the interference therefrom. Preferably the ozone is added in the photoionization chamber.

In the detection of nitric oxide in the presence of ammonia, an acid gas is added to the effluent gaseous stream and is reacted with the ammonia to remove the interference therefrom prior to passing the gases through the membrane. The acid gas may be sulphur dioxide or hydrogen chloride.

To compensate for the interference of varying or unknown quantities of oxygen in streams nearly oxygen free or having low levels, under about 10%, of oxygen, oxygen, preferably in air, is added to the gases to raise the oxygen level thereof above about 10%. Preferably the oxygen is added to the gases in the photoionization chamber.

Other objects, features and advantages of this invention will be apparent to those skilled in the art from the following detailed description of preferred embodiments thereof taken together with the accompanying drawings, in which.

Figure 1:
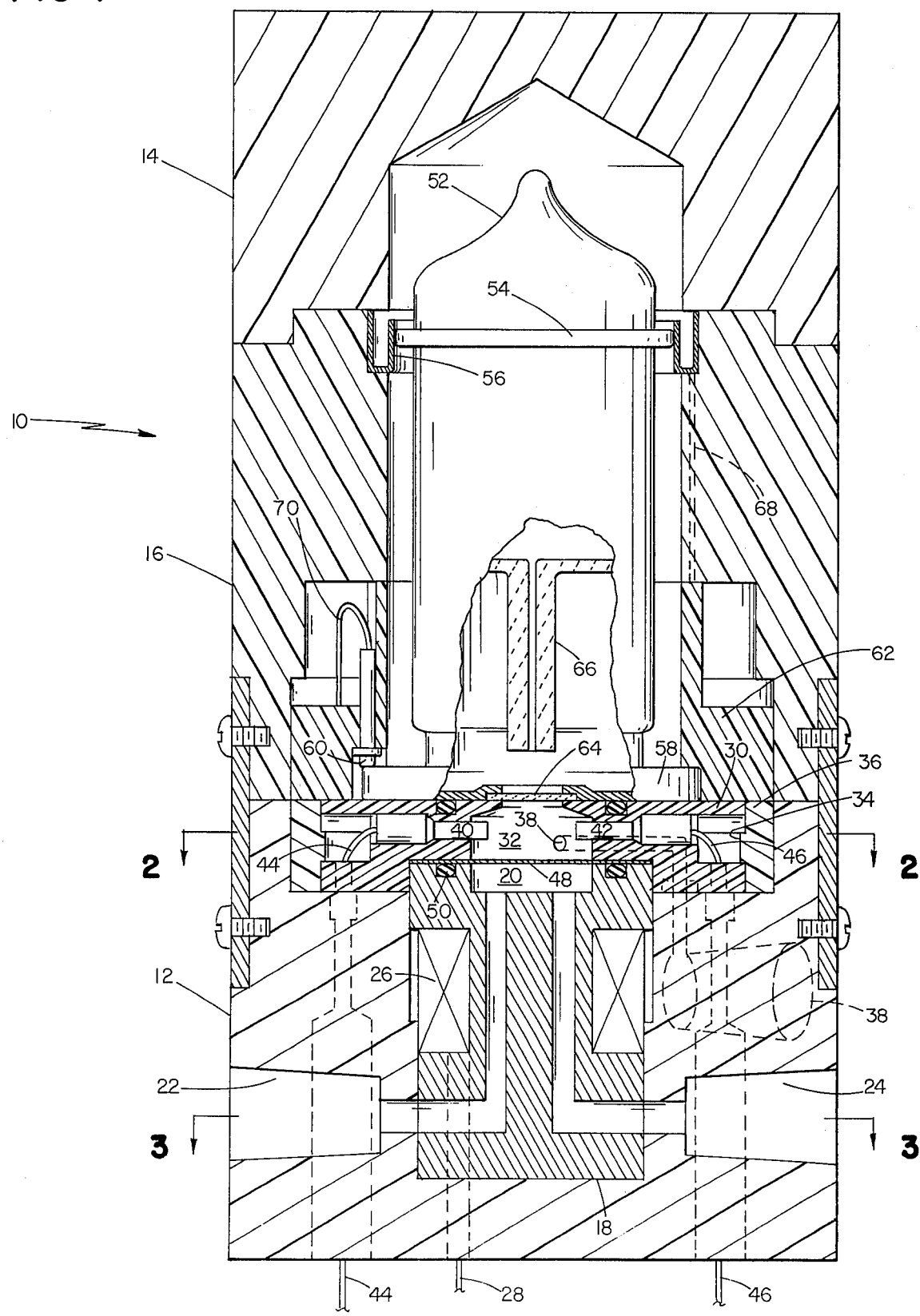
FIG. 1 is a sectional view in elevation of photoionization apparatus according to the invention.
Figure 2:
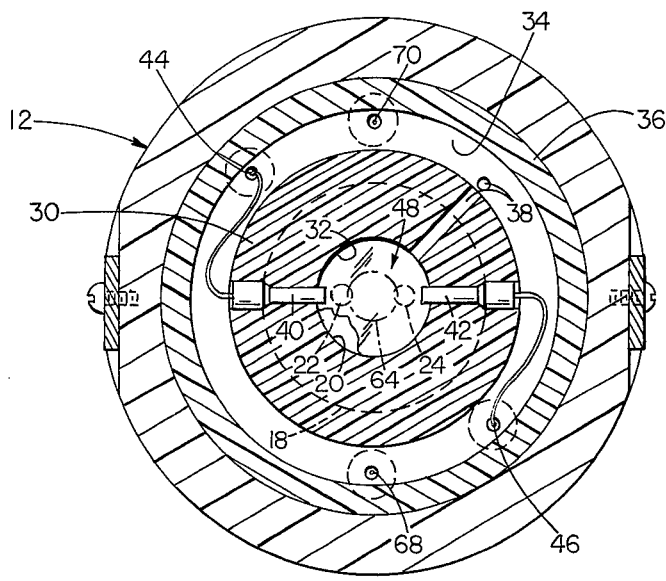
FIG. 2 is a reduced sectional view taken along the line 2—2 of FIG. 1.
Figure 3:
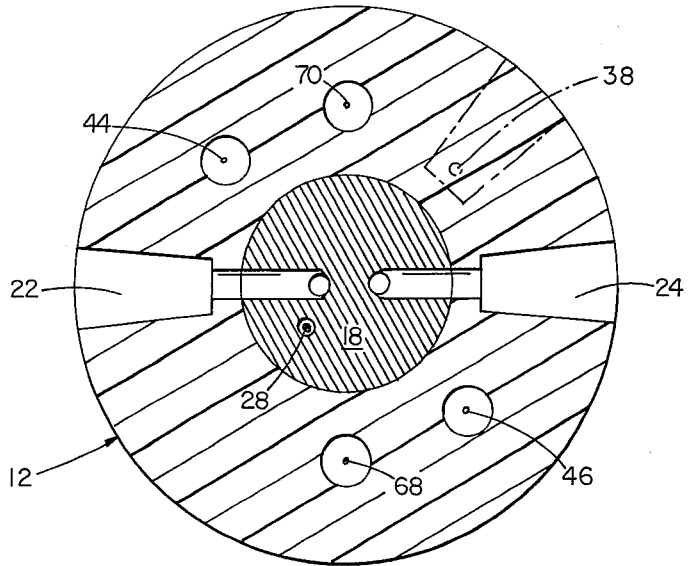
FIG. 3 is a reduced sectional view taken along the line 3—3 of FIG. 1.

With reference to FIGS. 1–3 of the drawings, the apparatus includes a housing 10 comprising a base 12, a cover 14 and an intermediate portion 16 therebetween.

Positioned within a central cavity in base 12 is a stainless steel ballast member 18. Ballast member 18 has a recess 20 in its upper surface defining a ballast chamber having a volume of about 0.32 cc. Inlet and outlet passages 22, 24, respectively, communicate through base 12 and member 18 with ballast chamber 20. An electric heating element 26 is positioned in an annular recess about member 18 adjacent inlet and outlet passages 22, 24, an electric cable 28 connected to a power supply (not shown) extending thereto through base 12 and member 18.

Also positioned within a cavity in base 12, above member 18 is a member 30 having a photoionization chamber 32 having a volume of about 0.80 cc. facing ballast chamber 20. An annular groove 34 extends about the circumference of member 30 and a collar 36 extends about groove 34 defining with groove 34 an annular chamber. A purge gas passage 38 communicates with photoionization chamber 32 through base 12, groove 34 and member 30. The opening through base 12 for purge gas passage 38, shown in broken lines in FIG. 1, is shown positioned above the openings for passages 22, 24 for convenience of illustration only. No outlet is provided for the purge gas since it will pass the membrane 48 to be described, into ballast chamber 20. Detection electrodes 40, 42 extend from groove 34 into chamber 32, the cables 44, 46 therefor extending to groove 34 through base 12 and member 30.

Ballast chamber 20 and photoionization chamber 32 are separated from each other by a gas permeable membrane 48 extending thereacross between members 18 and 30 having an effective area of about 1.26 cm² exposed to chambers 20, 32. An elastomeric O-ring 50 is positioned in an annular recess in the upper surface of member 18 about ballast chamber 20 tightly sealing membrane 48. The selection of a membrane depends on the particular use therefor. Where the primary purpose is to exclude particulates from the photoionization chamber, a 1 mil porous membrane with a pore size of 5–10 microns, such as porous teflon (polytetrafluoroethylene) sold by Millipore Corp., Bedford, Mass., or such as porous polyvinyl chloride, sold under the trademark Celgard by Celanese Corp., New York, N.Y., may be used. Where selective permeability is desired to exclude, as well, from the photoionization chamber high molecular weight organic materials, a 1 mil gas permeable, continuous membrane of dimethyl silicone sold by General Electric Co., Schenectady, N.Y., may be used.

Positioned within intermediate portion 16 of housing 10 and extending into cover 14, is a source 52 of monochromatic vacuum ultraviolet radiation, i.e., radiation in the range of 1200–1400 A producing energy levels of at least 8–10 eV. Such sources are low pressure gas filled lamps producing predetermined energy levels, e.g. $H_2$ (10.2 eV), Kr (10.0 eV), and Xe (9.5, 8.4 eV).

The source or lamp 52 has its anode 54 in contact with electrical connector 56 and its cathode 58 in contact with electrical connector 60 secured in retainer 62. Lamp 52 has an ultraviolet transmitting window 64, e.g., of magnesium fluoride or lithium fluoride, exposed to photoionization chamber 32. A glass capillary 66 is provided in lamp 52 to collimate the emission therefrom. Cables 68, 70 from connectors 56, 60 extend outwardly through intermediate portion 16 to a power supply (not shown).

Figure 4:
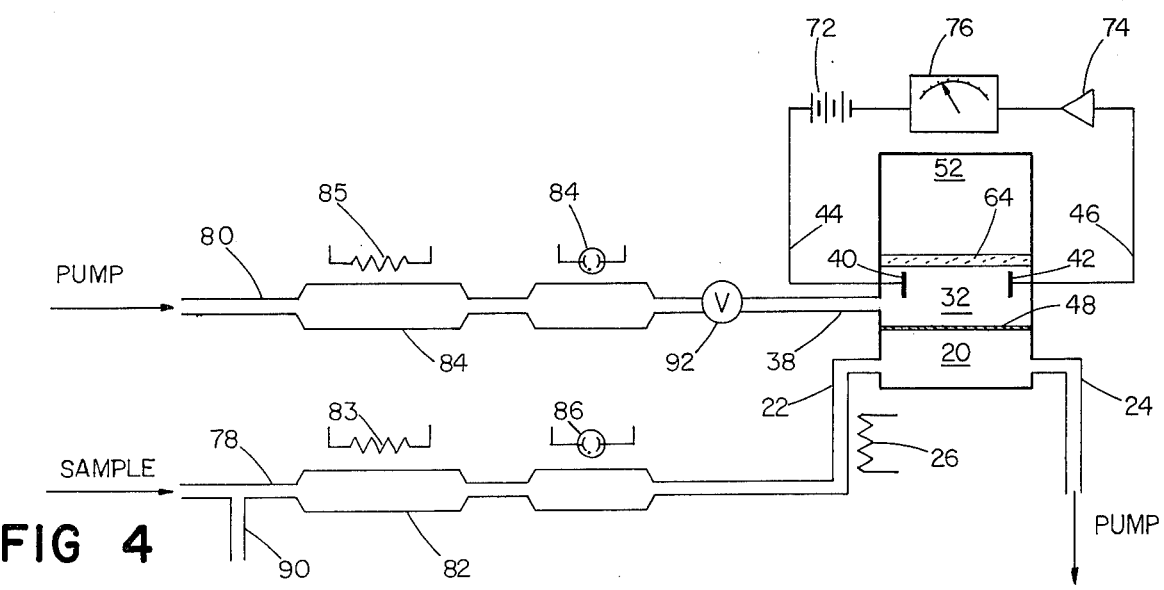
FIG. 4 is a schematic illustration of a system employing the invention.

As illustrated schematically in FIG. 4, electrodes 40, 42 in photoionization chamber 32 are connected to a power source 72 which positively biases electrode 42. As ionization proceeds in chamber 32 current flow is amplified by amplifier 74 and changes are indicated by signal processor 76 which may be of the meter type as illustrated or of the digital type.

As also illustrated in FIG. 4, inlet passage 22 and purge gas passage 38 respectively may have conduits 78, 80 connecting in series with each of inlet passage 22 and purge gas passage 38, combustion chambers 82, 84 containing platinized alumina pellets, and having heaters 83, 85 respectively thereadjacent, and sources of radiation 86, 88 in the 1849 A range such as mercury vapor lamps. Conduit 78 also has a branch conduit 90 connected thereto and a valve 92 is provided in conduit 80 adjacent purge gas passage 38.

The provision of the membrane 48 between the ballast and photoionization chambers 20, 32 effectively isolates the photoionization chamber 32 from the gaseous stream passed through ballast chamber 20. Gases from the stream are diffused through membrane 48 while any particulate matter in the stream is excluded from the photoionization chamber 32 thereby preventing any deposits from accumulating on window 64 with resultant attenuation of radiation emitted from lamp 52. The separation of the chambers 20, 32 further permits treatment of the gases either in the stream or in the photoionization chamber to enhance the selectivity of the process by the removal or separation of interfering species or by compensation therefor. During the operation of the apparatus heating element 26 is operated to heat the gases to 55°–60° C. as they enter ballast chamber 20 to prevent any moisture condensation particularly on membrane 48, which could interfere with diffusion of gases therethrough.

Determination Of NO In The Presence Of $NH_3$

Although nitric oxide (NO) and ammonia $NH_3$ have ionization potentials of 9.2 eV and 10.15 eV, respectively, no radiation source is presently available for distinguishing the two species. A 10 eV radiation source will respond to both species in a ratio of about 1:0.6 (NO:$NH_3$). To remove the interference of the ammonia and to permit accurate detection of nitric oxide, an acid gas such as $SO_2$ or HCl is added to the stream and reacted with the $NH_3$ converting the $NH_3$ to a non-interfering compound. It has been found, however, that if the reaction of the $NH_3$ with $SO_2$ is allowed to proceed in the photoionization chamber 32 a precipitate forms on the window 64 attenuating radiation and the signal resulting from the ionization of NO. Therefore, the $SO_2$ is added to the stream is conduit 78 through branch conduit 90 and the reaction with the $NH_3$ is allowed to proceed before the gases pass through membrane 48. Using a porous membrane, NO diffuses through the membrane, but no particulates form on window 64 and there is no attenuation of radiation or signal.

Determination Of $NH_3$ In The Presence Of NO

The reaction of nitric oxide (NO) with ozone ($O_3$) is employed to effectively remove the interference of NO when measuring $NH_3$. Thus an oxygen containing stream (air) is employed as a purge gas in photoionization chamber 32. The purge gas in conduit 80 is exposed to mercury vapor lamp 88 producing radiation in the region of 1849 A resulting in the production of ozone in the purge gas which is pumped into photoionization chamber 32. The $O_3$ reacts quickly with NO in chamber 32 to produce $NO_2$ which has a response of only about 3% of NO thus reducing interference to a tolerable level. The reaction of $NH_3$ with $O_3$ is slow and no significant reduction of signal results. As in the determination of NO in the presence of $NH_3$, a 10 eV radiation source and a porous membrane are employed. The membrane 48 permits the treatment with $O_3$ of only the small portion of the sample passing through the membrane. If the sample stream in conduit 78 contains significant quantities of oxygen, however, it is possible to pass the stream past mercury vapor lamp 86 to produce $O_3$ and thus to treat the entire sample.

Determination Of Inorganics In The Presence Of Hydrocarbons

Many hydrocarbons will respond to a 10 eV radiation source with a significantly higher response than inorganics such as NO and $NH_3$. Accordingly, to measure such inorganics it is necessary to remove any hydrocarbons from both the sample stream and from the purge gas. This is accomplished by passing the sample stream and the purge gas, respectively, in conduits 78, 80, through combustion chambers 82, 84 containing platinized alumina pellets heated by heaters 83, 85 to between 200°–300° C. The hydrocarbons contacting the platinum catalyst are thermally decomposed and oxidized to non-interfering species such as $CO_2$ and $H_2O$. To oxidize the hydrocarbons it is necessary that the gaseous streams contain oxygen which may be added ahead of the combustion chambers, if necessary. The determination of stable inorganics can then proceed.

Compensation For Oxygen Interference

Oxygen in the sample stream has the effect of quenching the signal resulting from ionization of many species. This is a particular problem in gases having variable, trace or small amounts of oxygen. Thus the rate of signal attenuation increases rapidly with the addition of small amounts of oxygen to an oxygen free stream and hence in such circumstances the signal is unreliable. It has been found, however, that above a certain level, signal attenuation from oxygen stabilizes. The signal produced by nitric oxide in the presence of from 10–20% oxygen changes only slightly. Thus, the addition of oxygen to the photoionization chamber 32 stabilizes signal attenuation due to variable oxygen content. Accordingly, to compensate for oxygen interference, the oxygen level in the photoionization chamber 32 is raised to above 10%, preferably about 20% by flowing air thereinto through purge gas passage 38. Air, as the purge gas, is flowed into chamber 32 at a rate of 20 cc/min., controlled by valve 92, and the sample gas is flowed through ballast chamber 20 at a rate of from 500–1000 cc/min. The oxygen in the sample stream can then vary from 0–20% without significant alteration of signal strength. Advantageously, the presence of membrane 48 avoids the necessity of treating and diluting the sample stream. Hydrocarbons are removed from the air prior to passage thereof into chamber 32, as above described.

Determination Of Organic Sulphur Compounds

Organic sulphur compounds have low ionization potentials and can be ionized by a 9.5 eV xenon source. Interference is encountered however from high molecular weight hydrocarbon materials such as terpenes. To minimize such interferences a continuous membrane of dimethyl silicone is employed between chambers 20, 32. Organic sulphur compounds, such as $CH_3SH$, $CH_3SSCH_3$, and $CH_3SCH_3$, have high diffusivities through such a membrane as compared to high molecular weight hydrocarbons. Thus, using a 9.5 eV radiation source and a dimethyl silicone membrane, organic sulphur compounds can be measured despite the presence of high molecular weight hydrocarbons in the sample stream.

It has been found that $H_2S$ can be detected with the organic sulphur compounds aforementioned, using a 10.0 eV krypton source or a 10.2 eV hydrogen source.

Determination Of Aromatic Hydrocarbons

Aromatic hydrocarbons have substantially higher diffusivities through a dimethyl silicone membrane than paraffins and aliphatic hydrocarbons. Specific measurement of aromatics with paraffins and aliphatics in the sample stream is made employing a 9.5 eV radiation source and a dimethyl silicone membrane.

Other embodiments of this invention will occur to those skilled in the art which are within the scope of the following claims.

What is claimed is:

1. In photoionization apparatus, comprising:
   a housing having a chamber therein;
   a gas inlet passage and a gas outlet passage, each said passage extending through said housing and communicating with said chamber;
   a radiation source exposed to said chamber; and detection electrodes in said chamber;
   the improvement in which:
   a gas permeable organic plastic membrane extends across said chamber dividing said chamber into two subchambers, a ballast chamber on one side of said membrane and a photoionization chamber on the other side of said membrane;
   said inlet and outlet passages extending through said housing and communicating with said ballast chamber; and
   said electrodes positioned in and said radiation source exposed to said photoionization chamber.

2. The improvment claimed in claim 1 further including heating means positioned in said housing adjacent said inlet and outlet passages.

3. The improvement claimed in claim 1 in which said membrane is porous.

4. The improvement claimed in claim 1 further including a gas conduit connected with said gas inlet passage, said gas conduit including in series therewith a source of radiation for the conversion of oxygen to ozone.

5. The improvement claimed in claim 1 further including a gas conduit line connected with said gas inlet passage, said gas conduit line having a branch conduit line connected thereto for the introduction of reactant gases into said gas conduit line.

6. The improvement claimed in claim 1 further including a gas conduit connected with said gas inlet passage, said gas conduit including in series therewith a combustion chamber containing catalytic material for the conversion of hydrocarbons to non-interfering species, and further including heating means adjacent said combustion chamber.

7. The improvement claimed in claim 6 in which said catalytic material comprises platinum.

8. The improvement claimed in claim 1 in which said membrane is continuous.

9. The improvement claimed in claim 4 in which said membrane comprises dimethyl silicone.

10. The improvement claimed in claim 1 further including a purge gas passage extending through said housing and communicating with said photoionization chamber.

11. The improvement claimed in claim 10 further including a purge gas conduit connected with said purge gas passage, said purge gas conduit including in series therewith a source of radiation for the conversion of oxygen to ozone.

12. The improvement claimed in claim 10 further including a purge gas conduit connected with said purge gas passage, said purge gas conduit including in series therewith a combustion chamber containing catalytic material for the oxidation of hydrocarbons, and further including heating means adjacent said combustion chamber.

13. The improvement claimed in claim 12 in which said catalytic material comprises platinum.

14. In the method of selective photoionization of a component in a gaseous stream in which gases from said stream are passed through a photoionization chamber, radiant energy of a predetermined level is passed through said chamber with said gases therein, and ionization of said component is detected at detector electrodes in said chamber, the improvement in which
   said gaseous stream is passed through an inlet into a ballast chamber and is passed through an outlet out of said ballast chamber, a portion of said gases from said stream being diffused from said ballast chamber into said photoionization chamber through a gas permeable organic plastic membrane.

15. The method claimed in claim 14 further including the step, prior to passing said gases into said photoionization chamber, of heating a catalyst effective to assist in the oxidation of hydrocarbon compounds in said gaseous stream and contacting said gaseous stream with said catalyst oxidizing said hydrocarbon compounds.

16. The method claimed in claim 15 in which said catalyst is platinum.

17. The method claimed in claim 14 in which said component is ammonia ($NH_3$) and said gases include ammonia ($NH_3$) and nitric oxide (NO), said method further including the steps of introducing ozone ($O_3$) into said gases, reacting said nitric oxide (NO) with said ozone ($O_3$) and thereafter detecting said ammonia ($NH_3$).

18. The method claimed in claim 17 in which said ozone is introduced into said gases in said photoionization chamber.

19. The method claimed in claim 14 in which said component is nitric oxide (NO) and said gases include nitric oxide (NO) and ammonia ($NH_3$), said method further including the step, prior to passing said gases into said photoionization chamber, of adding an acid gas to said gaseous stream and reacting said acid gas with said ammonia ($NH_3$).

20. The method claimed in claim 19 in which said acid gas is sulfur dioxide ($SO_2$).

21. The method claimed in claim 19 in which said acid gas is hydrogen chloride (HCl).

22. The method claimed in claim 14 in which said gases include less than about 10% oxygen ($O_2$), said method further including the step of introducing oxygen ($O_2$) as a separate purge gas directly into said photoionization chamber in an amount sufficient to raise the level of oxygen ($O_2$) in said photoionization chamber to a level above about 10%.

23. The method claimed in claim 22 in which oxygen is introduced into said photoionization chamber in air.

24. The method claimed in claim 23 further including the step, prior to introducing said air into said photoionization chamber, of heating a catalyst effective to assist in the oxidation of hydrocarbon compounds in said air and contacting said air with said catalyst oxidizing said hydrocarbon compounds.

25. The method claimed in claim 23 in which said catalyst is platinum.

* * * * *